United States Patent
Rathjen

(10) Patent No.: US 9,411,938 B2
(45) Date of Patent: Aug. 9, 2016

(54) SYSTEM FOR DEFINING CUTS IN EYE TISSUE

(75) Inventor: Christian Rathjen, Bremen (DE)

(73) Assignee: SIE AG, SURGICAL INSTRUMENT ENGINEERING (CH)

( * ) Notice: Subject to any disclaimer, the term of this patent is extended or adjusted under 35 U.S.C. 154(b) by 738 days.

(21) Appl. No.: 12/731,573

(22) Filed: Mar. 25, 2010

(65) Prior Publication Data

US 2010/0256965 A1 Oct. 7, 2010

Related U.S. Application Data

(60) Provisional application No. 61/166,058, filed on Apr. 2, 2009.

(51) Int. Cl.
*A61F 9/008* (2006.01)
*G06F 19/00* (2011.01)

(52) U.S. Cl.
CPC ........ *G06F 19/3437* (2013.01); *A61F 9/00831* (2013.01); *A61F 9/00836* (2013.01); *A61F 9/00827* (2013.01); *A61F 2009/0087* (2013.01); *A61F 2009/00853* (2013.01); *A61F 2009/00863* (2013.01); *A61F 2009/00865* (2013.01); *A61F 2009/00872* (2013.01); *A61F 2009/00897* (2013.01); *G06F 19/3481* (2013.01)

(58) Field of Classification Search
CPC .............. A61B 19/50; A61B 2019/507; A61F 9/008–9/009; A61F 2009/008–2009/00897; G06F 19/3437
USPC .......... 606/4–6, 10, 11, 12; 128/898; 382/128
See application file for complete search history.

(56) References Cited

U.S. PATENT DOCUMENTS 5,549,632 A * 8/1996 Lai ..................................... 606/5
5,891,131 A * 4/1999 Rajan et al. ....................... 606/5
(Continued)

FOREIGN PATENT DOCUMENTS

DE 4304571 2/1993

OTHER PUBLICATIONS

Sagar, M. A., Bullivant, D., Mallinson, G. D., Hunter, P. J., and Hunter, I. W., A virtual environment and model of the eye for surgical simulation, Proceedings of SIGGRAPH Annual Computer Graphics Conference 1994, Orlando, Florida, Jul. 24-29, pp. 205-211.*

*Primary Examiner* — William Thomson
*Assistant Examiner* — Nathan J Jenness
(74) *Attorney, Agent, or Firm* — Ostrolenk Faber LLP

(57) ABSTRACT

A computer-aided system include a data storage (18) with eye data (181), which defines a three-dimensional model of the eye, and a reference generator (113) for defining and storing a geometric reference in relation to the three-dimensional model of the eye. The system additionally includes a cut surface editor for defining and positioning cut surfaces in the three-dimensional model of the eye based on user instructions. Finally, the system includes a cut pattern generator (117) for, based on the positioned cut surfaces, generating and storing three-dimensional cut patterns for defining tissue cuts to be executed in a human eye by means of femtosecond laser pulses. The generation of a three-dimensional cut pattern permits the user to define tissue cuts made possible by femtosecond laser pulses in a targeted and efficient fashion in the three-dimensional model of the eye without having to undertake manipulations directly on the eye for this purpose.

16 Claims, 10 Drawing Sheets

(56) References Cited

U.S. PATENT DOCUMENTS

| | | | |
|---|---|---|---|
| 6,099,522 A * | 8/2000 | Knopp et al. | 606/10 |
| 6,210,401 B1 * | 4/2001 | Lai | 606/12 |
| RE37,585 E | 3/2002 | Mourou et al. | |
| 6,436,093 B1 * | 8/2002 | Ruiz et al. | 606/5 |
| 2007/0173793 A1 * | 7/2007 | Rathjen | 606/4 |
| 2008/0039825 A1 * | 2/2008 | Lai | 606/5 |
| 2008/0082088 A1 * | 4/2008 | Kurtz et al. | 606/5 |
| 2008/0319428 A1 | 12/2008 | Wiechmann et al. | |

\* cited by examiner

SYSTEM FOR DEFINING CUTS IN EYE TISSUE

CROSS-REFERENCE TO RELATED APPLICATIONS

This application claims benefit of and priority to U.S. Provisional Patent Application No. 61/166,058 filed Apr. 2, 2009, the entire contents of which are hereby incorporated by reference herein.

BACKGROUND

1. Field of the Disclosure

The present disclosure relates to a system for defining cuts in eye tissue. The present disclosure relates to, in particular, a computer-aided system for defining one or more tissue cuts to be executed in a human eye by means of femtosecond laser pulses.

2. Related Art

Laser technology has been propagated for decades for universal use in cutting very different materials. However, in the field of ophthalmology, the laser has yet to replace the scalpel for cutting eye tissue in a number of applications. That is to say, the known laser systems do not allow a user to generate more or less arbitrary cuts in the eye tissue, as described in e.g. WO9425107 or WO9409849, which are possible using e.g. a scalpel. Even if a femtosecond laser moreover affords the possibility of executing cuts in the eye tissue which cannot be done using a scalpel (e.g. puncture-free cuts within the tissue) by means of femtosecond laser pulses, the known opthalmological laser systems are very limited in respect of the cutting flexibility available to the user. In particular, the reason for this is also that there are a multiplicity of ineffective and possibly even patient-damaging parameterizations of the laser system for a cut result wanted by the user. The known opthalmological laser systems afford the users limited cutting flexibility because the typical user is not an expert in the field of lasers and is generally unable to efficiently and safely execute the beam deflection and pulse control of a laser. The known opthalmological laser systems in general permit neither operation planning with simple recognition or prevention of damaging or impossible cutting guides, nor minimizing the intervention time or automatic generation of a cutting sequence. Finally, the known opthalmological laser systems also do not allow the treatment of an eye based on previously executed and established interventions, which are not part of standard procedures, such as the cutting of a corneal flap.

SUMMARY

It is an object of the present disclosure to propose a computer-aided system for defining one or more tissue cuts to be executed in a human eye by means of femtosecond laser pulses, which does not have at least some of the disadvantages of the known systems. In particular, it is an object of the present invention to propose a computer-aided system for defining the tissue cuts which make the cutting flexibility allowed by femtosecond laser technology available to a user. In particular, it is a further object of the present invention to propose a computer-aided system for defining tissue cuts on the basis existing definitions of established tissue cuts.

According to the present invention, these objects are achieved in particular by the elements of the independent claims. Further advantageous embodiments additionally emerge from the dependent claims and the description.

The present invention achieves the abovementioned objects in particular by virtue of the fact that provision is made for a computer-aided system for generating a three-dimensional cut pattern which defines one or more tissue cuts to be executed in a human eye by means of femtosecond laser pulses. The computer-aided system comprises a data storage with eye data, which defines a three-dimensional model of the eye, and a reference generator, which is configured to define and to store at least one geometric reference in relation to the three-dimensional model of the eye. Moreover, the computer-aided system comprises a cut surface editor, which is configured to define, based on user instructions, at least one cut surface and to position the at least one cut surface in the three-dimensional model of the eye in relation to the at least one geometric reference. Finally, the computer-aided system comprises a cut pattern generator, which is configured to generate and to store the three-dimensional cut pattern for defining tissue cuts based on the at least one or more cut surfaces positioned in the three-dimensional model of the eye. Defining tissue cuts in an eye by generating a three-dimensional cut pattern, which is based on at least one or more cut surfaces determined and positioned by the user in a three-dimensional model of the eye, makes the cutting flexibility afforded by femtosecond laser technology for single or multiple use in one or more eye treatments available to the user since the tissue cuts can be defined preliminarily in a targeted and efficient fashion in the three-dimensional model of the eye and, in return, configurations, manipulations or interventions are not required during surgical treatment directly on the eye.

In an embodiment variant, the cut surface editor is configured to define the at least one cut surface on the basis of a user-defined cutting line and a user-defined cutting line trajectory. As a result of this, a user is able to define, flexibly based on a cutting line, cut surfaces which have varied shapes and which are guided through the eye tissue along the cutting line trajectory like a blade or a wire cutter when the cut is executed.

In a further embodiment variant, the cut surface editor is configured to define the at least one cut surface on the basis of at least one surface element, which can be selected from a list of a plurality of different surface elements on the basis of user instructions. This affords a simple definition of predefined cutting shapes, which moreover can still be adapted by the user.

In an embodiment variant, the computer-aided system comprises an applicator selector, which is configured to determine, based on user instructions, an application element which should be applied to the eye when executing the tissue cuts, and a deformation module, which is configured to determine, based on the eye data and the determined application element, a deformed three-dimensional model of the eye, representing the eye in the applied application element state. In an embodiment variant, the reference generator is configured to define and to store the geometric reference in relation to the deformed three-dimensional model of the eye; the cut surface editor is configured to position the at least one cut surface in relation to the at least one geometric reference in the deformed three-dimensional model of the eye; and the cut pattern generator is configured to generate and to store the three-dimensional cut pattern on the basis of the at least one or more cut surfaces positioned in the deformed three-dimensional model of the eye. That is to say, cut patterns can be generated which are based on cut surfaces defined directly in the deformed state of the model of the eye. In a further embodiment variant, the deformation module is configured, based on the three-dimensional cut pattern and the determined application element, to determine a deformed three-dimensional cut pattern, which is based on a deformed state of the at least one or more cut surfaces positioned in the three-dimensional model of the eye, with the deformed state being defined by the deformed three-dimensional model of the eye. That is to say, deformed cut patterns can be generated based on cut surfaces, which were defined in the non-deformed state of the model of the eye. The deformation module thus allows adapting the model of the eye to the state of the eye when the application element is attached thereto and transforming cut surfaces and/or geometric references, already defined in the non-deformed state, into the deformed state, or defining new or additional cut surfaces and/or geometric references directly in the deformed state.

In an embodiment variant, the computer-aided system comprises a sequence generator, which is configured to determine, automatically or based on user instructions, an execution sequence for the cut surfaces of the tissue cuts defined in the three-dimensional cut pattern, wherein a cut surface which, according to the execution sequence, is to be generated earlier is prevented from covering or shadowing focused radiation of the femtosecond laser pulses for generating a cut surface which, according to the execution sequence, is to be generated later. In a further embodiment variant, the sequence generator is configured to determine a covering or shadowing of a cut surface to be generated later by a cut surface to be generated earlier on the basis of a beam cone defined by focused radiation of the femtosecond laser pulses. The sequence generator therefore affords a plausibility check of the sequence in which the cut surfaces of a cut pattern are executed based on shadowing and/or covering by cut surfaces.

In a further embodiment variant, the sequence generator is configured to determine the execution sequence for the cut surfaces such that an expected thermal stress on the eye does not exceed a defined threshold. The sequence generator thus prevents undesired damage to eye tissue as a result of overloading.

In an embodiment variant, the computer-aided system comprises a mask selector, which is configured to determine, based on user instructions, a projection mask to be positioned in front of the eye when executing the tissue cuts and to check, based on the determined projection mask and a beam cone defined by focused radiation of the femtosecond laser pulses, whether the cut surfaces of the tissue cuts defined in the three-dimensional cut pattern can be generated without shadowing by the projection mask. Hence, the mask selector allows a plausibility check of the cut pattern in relation to an undesired shadowing of cut surfaces by a selected projection mask.

In a further embodiment variant, the computer-aided system comprises a visualization module, which is configured to display, based on the eye data, a visualization of the eye and a beam cone, defined by focused radiation of the femtosecond laser pulses, on a display; and a cut recorder, which is configured, based on user instructions, to generate a virtual tissue cut in the visualized eye by moving the beam cone and to store the virtual tissue cut as a three-dimensional cut pattern. Hence, the cut recorder allows the user to define a cut surface and/or a cut pattern by executing a virtual tissue cut in the visualized model of the eye.

In an embodiment variant, the computer-aided system comprises a cut simulator, which is configured to simulate, based on the eye data and the stored three-dimensional cut pattern, executing the tissue cuts defined by the three-dimensional cut pattern and to visualize it on a display; and a cut pattern editor, which is configured to adapt, based on user instructions, the stored three-dimensional cut pattern using one or more operations from the following list: repositioning a cut surface, reorienting a cut surface, changing a cut direction of a cut surface, deleting a cut surface, deleting a cut surface component, changing a cut surface, adding a cut surface, duplicating a cut surface, changing a geometric reference, changing an execution sequence for the cut surfaces, changing an application element to be attached to the eye when executing the tissue cuts, changing a projection mask to be positioned in front of the eye when executing the tissue cuts and changing a beam cone defined by focused radiation of the femtosecond laser pulses. Hence, the cut simulator allows checking the effects of changes in the three-dimensional cut pattern by simulation; for example, differently shaped application elements can be checked and tested in relation to their effect in respect of refractive correction.

In a further embodiment variant, the cut pattern generator is configured to define tissue cuts in the three-dimensional cut pattern by one or more cut surfaces positioned in relation to a geometric reference, wherein a cut surface is in each case defined by one or more parameters from the following list: position, cutting line, cutting line trajectory, direction of cut, surface element class, surface element dimensions, surface element curvature and surface element orientation, and wherein an execution sequence is assigned to the cut surfaces.

In an embodiment variant, the cut pattern generator is configured to define the cut surfaces in the three-dimensional cut pattern in the form of macroinstructions. Depending on the design of the opthalmological laser device, the control thereof is carried out directly by means of the macroinstructions or on the basis of corresponding pulse grid instructions which control the femtosecond laser.

In a further embodiment variant, the cut surface editor is configured to adapt, based on user instructions, the at least one cut surface using one or more operations from the following list: scaling the size of the cut surface, delimiting the cut surface along one or more boundary lines, changing a curvature of the cut surface, changing an orientation of the cut surface, changing a cut direction of the cut surface and changing a cut class of the cut surface, wherein the cut class is defined by one or more elements of the following list of cut classes: cuts with a cut surface defined as a second order surface, cuts with a cut surface defined as a spline surface, cuts with a cut surface defined by a cutting line and cutting line trajectory and cuts with a cut surface defined by a stored three-dimensional cut pattern.

BRIEF DESCRIPTION OF THE DRAWINGS

In the following text, an embodiment of the present invention will be described based on an example. The exemplary embodiment will be illustrated by the following attached figures.

DETAILED DESCRIPTION OF THE EMBODIMENTS

Figure 1:
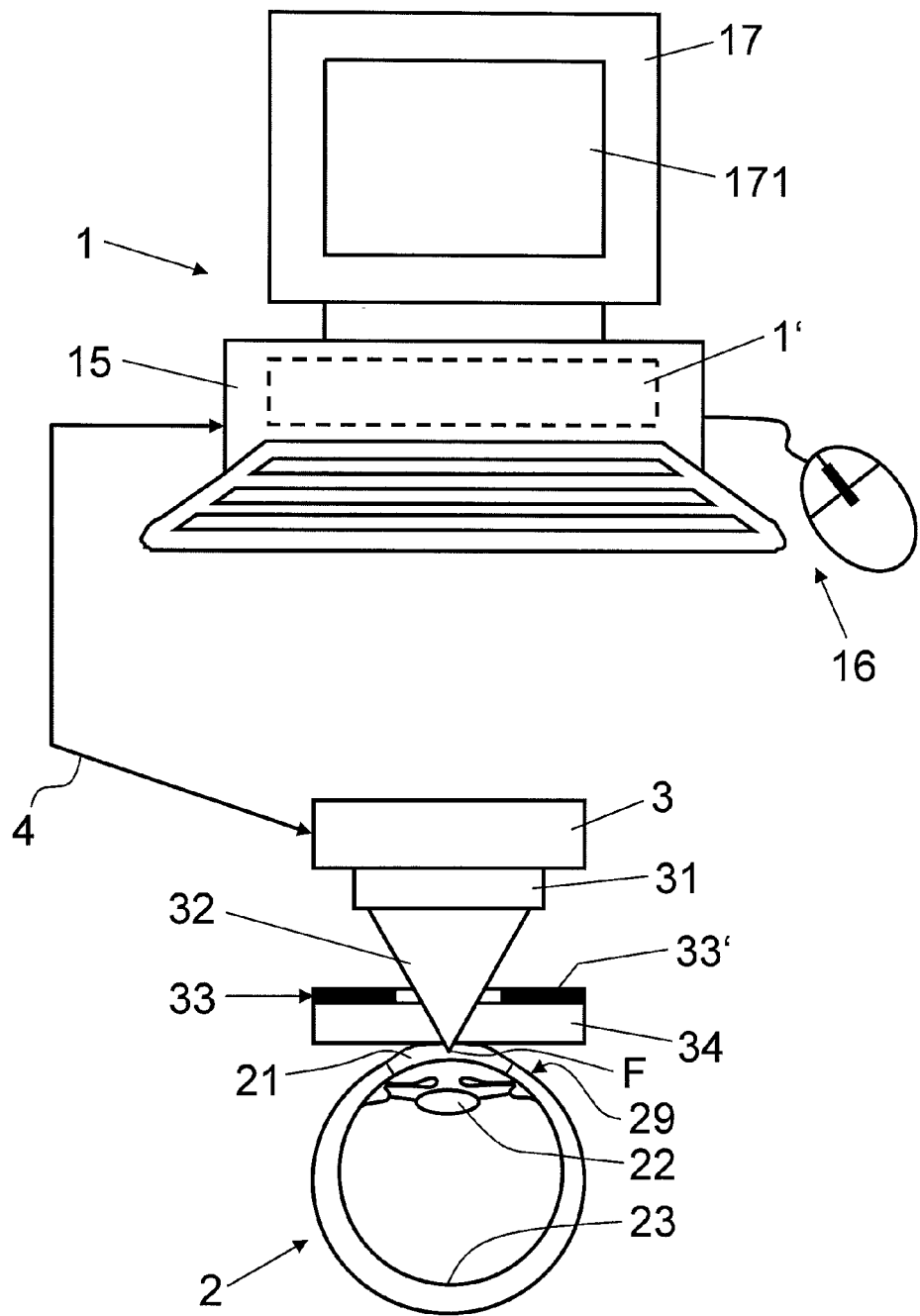
FIG. 1 schematically shows a computer system for generating a three-dimensional cut pattern which is connected to a laser device for executing tissue cuts on a human eye.

In FIG. 1, the reference sign 1 relates to a computer system for generating a three-dimensional cut pattern, defining one or more contiguous or separate tissue cuts in a human eye 2, which is/are to be executed by an opthalmological laser device 3 by means of femtosecond laser pulses.

The laser device 3 comprises a light projector 31, which focuses the femtosecond laser pulses onto or into the eye tissue in a defined beam cone 32. Here, a cut is respectively understood to be tissue decomposition or tissue decay, in a contiguous region of the eye tissue, which is typically effected by the femtosecond laser pulses at least two different focal points F. In the preferred applications, the eye tissue comprises various eye structures, in particular the cornea 21, the sclera 29, the lens 22 and the retina 23.

As illustrated in FIG. 1, the treatment is typically executed in a state of the eye 2 defined by the attachment of an application element 34. The application element 34 is a contact body, with a concave, convex or plane design, which deforms, e.g. makes applanate, the eye 2, particularly the cornea 21, into a desired intended state. Additionally, depending on the application, a projection mask 33, having opaque or light-damping mask regions 33', is positioned in front of the eye 2; said mask shadows the eye 2 from the beam cone 32 and penetration of the femtosecond laser pulses onto or into the eye tissue is prevented or damped. Attachment means such as suction rings for affixing the application element 34 and/or the projection mask 33 are not illustrated and are not described in any more detail herein.

The computer system 1 comprises one or more computers 15 with input elements 16 and a display 17. The input elements 16 for example comprise keys and positioning elements such as a computer mouse, a touchpad or a trackball. The input elements 16 and the display 17 can also be combined in a touch-sensitive screen. By way of example, the computer 15 is an operational mobile or fixedly installed PC with one or more processors, data storage and program storage.

Figure 2:
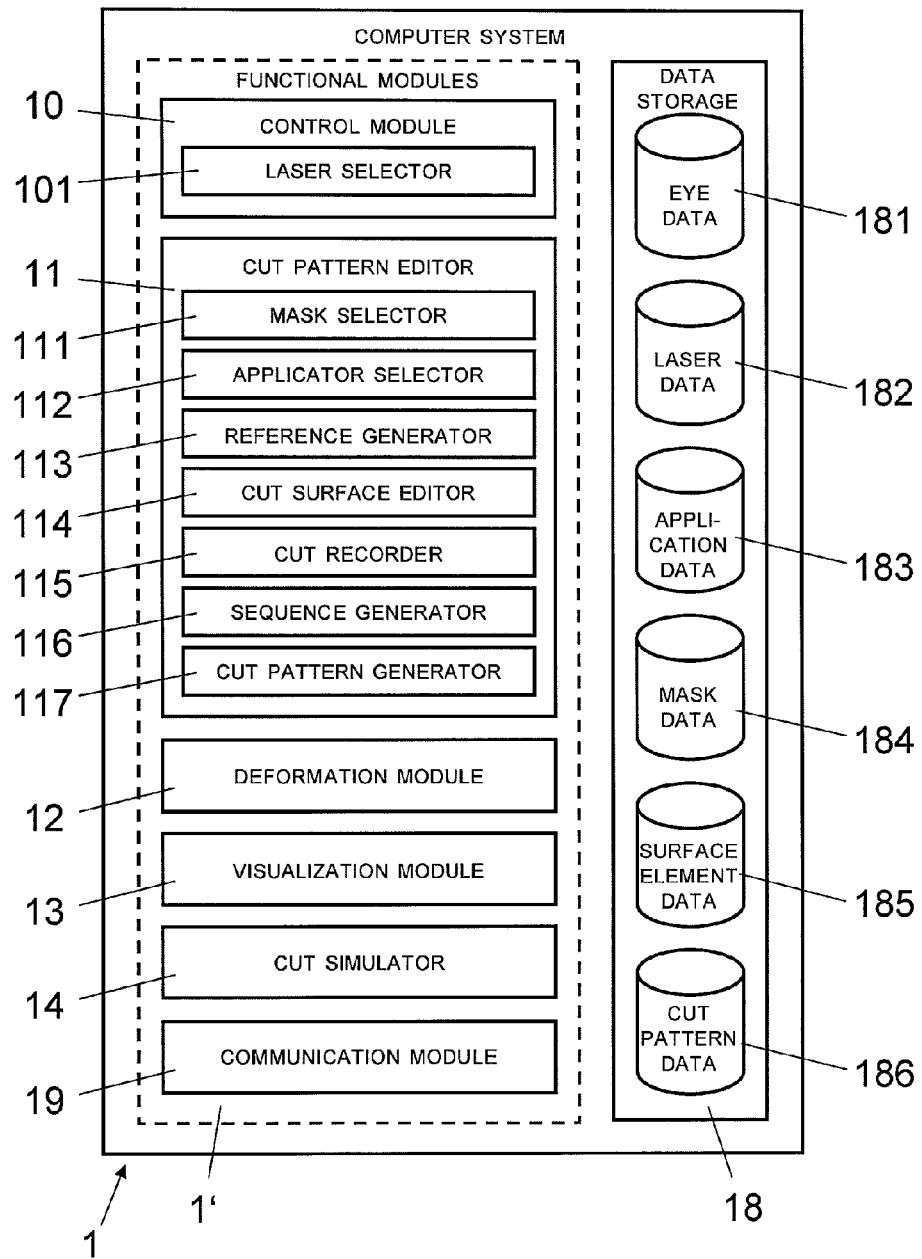
FIG. 2 shows a block diagram which schematically illustrates functional modules and data storage of the computer system for generating a three-dimensional cut pattern of the tissue cuts.

As illustrated schematically in FIG. 2, the computer system 1 comprises a plurality of functional modules 1', in particular a control module 10, a laser selector 101, a cut pattern editor 11, a deformation module 12, a visualization module 13, a cut simulator 14 and a communication module 19. The cut pattern editor 11 comprises a mask selector 111, an applicator selector 112, a reference generator 113, a cut surface editor 114, a cut recorder 115, a sequence generator 116 and a cut pattern generator 117. The functional modules 1' are preferably designed as programmed software modules, which are stored on a computer-readable data storage medium, which, fixedly or removeably, is connected to the computer system 1, and comprise computer program code for controlling the processors of the computer 15 such that said computer executes the subsequently described functions. A person skilled in the art will understand that in alternative embodiment variants the functional modules 1' can be designed partly or wholly as hardware elements.

The computer system 1 moreover comprises a data storage 18 with data structures for storing eye data 181 which defines a three-dimensional model of the eye, laser data 182 which defines various types and configurations of opthalmological laser devices 3, application data 183 which defines various application elements, mask data 184 which defines various projection masks, surface element data 185 which defines various surface elements, and cut pattern data 186 which defines various three-dimensional cut patterns. The data structures for storing the eye data 181 moreover comprise optional data structures for storing external measurement data and image data, which are for example imported from external measurement equipment or imaging equipment via a communication channel or are entered via the user interface 171 and are assigned to an eye 2 of a patient. In particular, the image data also comprises obfuscations and inclusions, which are superposed visually and are used for defining geometric references.

The communication module 19 is configured to interchange data, in particular cut pattern data, with an external computer-based data server over a telecommunication network, in particular over the Internet.

Figure 18:
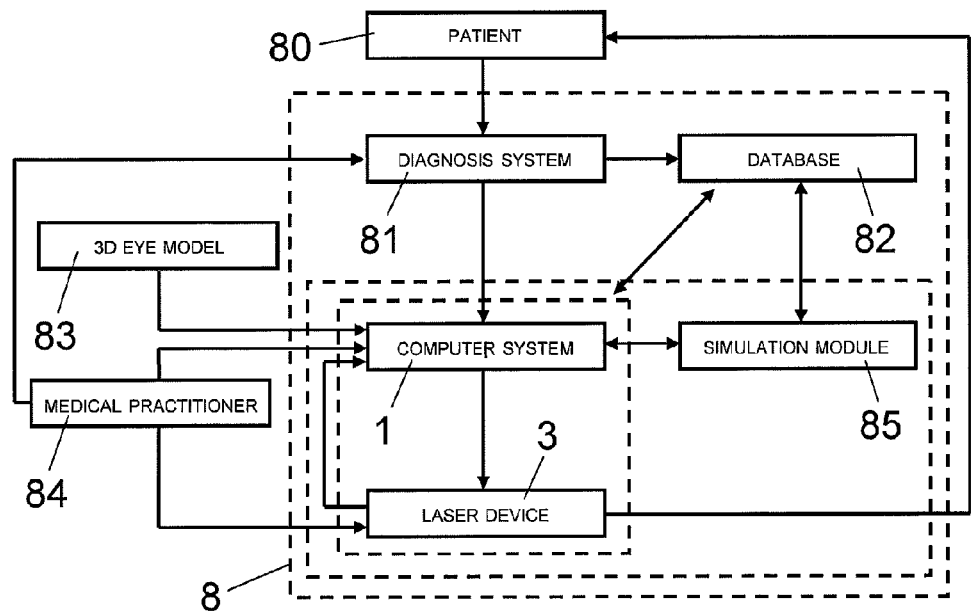
FIG. 18 shows a block diagram and data flowchart, which schematically illustrates an arrangement of the computer system for generating the cut pattern as part of a computer-aided operation planning system.

FIG. 18 illustrates an arrangement of the computer system 1 for generating a three-dimensional cut pattern as part of a (superordinate) computer-aided operation planning system 8. As illustrated in FIG. 18, in addition to the computer system 1, the operation planning system 8 comprises a plurality of additional computer-aided systems and/or modules, in particular a diagnosis system 81, a database 82 and a simulation module 85. A medical practitioner 84 controls the diagnosis system 81, which generates diagnosis data for the computer system 1 based on measurements and data on or from a patient 80. The diagnosis data is stored in the database 82 and supplied to the computer system 1 for generating a three-dimensional cut pattern. The cut pattern is generated according to instructions from the medical practitioner 84, which are based on a (three-dimensional) model of the eye 83. The simulation module 85 simulates a planned treatment on the basis of the defined cut pattern and laser data from the database 82, with, in addition to the mechanical change of the eye 2, optical properties of the eye 2 in particular also being determined as a result of the refractive correction of the eye 2 defined by the cut pattern. For the actual treatment of an eye 2 (from a donor or on the patient 80), the cut pattern is supplied to the laser device 3 from the computer system 1.

In the following sections, the various functions of the functional modules of the computer system 1 are described with reference to FIG. 3.

After the computer system 1 has been started up, a graphical user interface 171, which can be operated by the input elements 16, is presented to the user on the display 17 by the control module 10.

Figure 4:
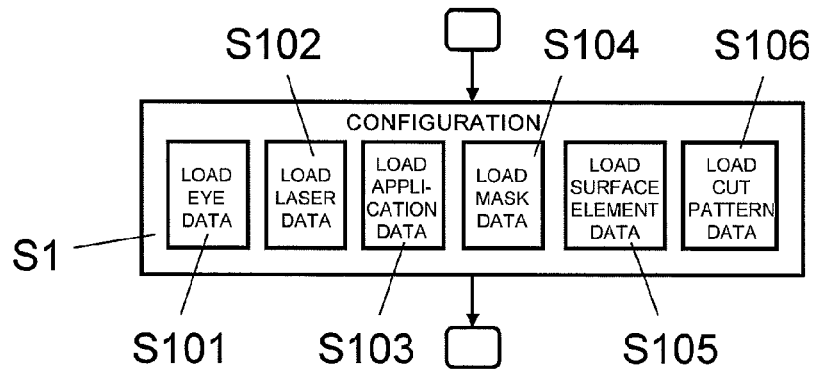
FIG. 4 shows a flowchart which illustrates a possible sequence of user-selected configuration steps and preliminary steps.

In optional step S1, the control module 10 executes user-selected configuration steps and preliminary steps, which are described in the following text with reference to FIG. 4.

In step S101, the control module 10 loads eye data 181 for one or more three-dimensional models of the eye and stores said data in the data storage 18. The models of the eye are generic or precise, patient-specific models of the eye. The eye data 181 is imported as available eye files or is defined via the user interface 171, for example in the form of measured values as eye parameters.

In step S102, the control module 10 loads laser data 182 for one or more opthalmological laser devices 3 and stores said data in the data storage 18. The laser data 182 is imported as available laser files for known laser devices 3, read from the opthalmological laser device 3 via a communication channel 4 and/or defined via the user interface 171 in the form of entered laser parameters. The laser parameters comprise pulse energy, pulse width, maximum pulse intensity (different values of the pulse intensity with otherwise unchanging pulse width and pulse energy emerge depending on the pulse shape), pulse rate, pulse spacings (grid data), wavelength, size of the focus, focal distance, mean laser power and/or numerical aperture of the opthalmological laser devices 3.

In step S103, the control module 10 loads application data 183 for one or more application elements 34 and stores said data in the data storage 18. The application data 183 is imported as available application files for known application elements 34, read from the opthalmological laser device 3 via a communication channel 4 and/or defined via the user interface 171 in the form of entered application parameters. By way of example, the application parameters comprise specifications in respect of thickness, shape and/or transmission characteristics.

In step S104, the control module 10 loads mask data 184 for one or more projection masks 33 and stores said data in the data storage 18. The mask data 184 is imported as available mask files for known projection masks 33, read from the opthalmological laser device 3 via a communication channel 4 and/or defined via the user interface 171 in the form of entered mask parameters. By way of example, the mask parameters comprise specifications in respect of the shape and the transmission characteristics.

In step S105, the control module 10 loads surface element data 185 for a plurality of surface elements and stores said data in the data storage 18. The surface element data 185 is preferably imported as an available surface element file for a library or list of known surface elements. The surface elements comprise, in particular, second order surface elements, e.g. planar surface elements, cone-shaped surface elements, Cylindrical surface elements or spherical surface elements, and spline surface elements and surface elements which are defined by a cutting line and a cutting line trajectory (in one variant, the cutting line trajectory comprises a twist).

In step S106, the control module 10 loads cut pattern data 186 for one or more three-dimensional cut patterns and stores said data in the data storage 18. The cut pattern data 186 is preferably imported as available cut pattern files, e.g. from a data storage medium, or is obtained by means of the communication module 19 via a telecommunication network from an Internet-based web server, which makes stored cut pattern files available for reuse.

Figure 3:
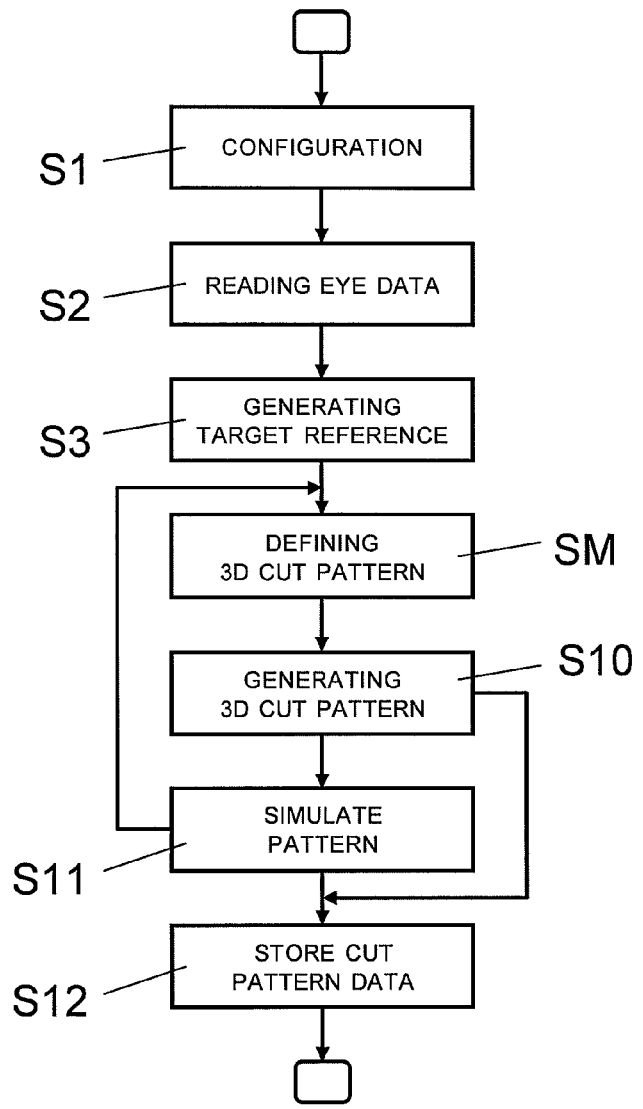
FIG. 3 shows a flowchart which illustrates a possible sequence of steps for generating the three-dimensional cut pattern.

As illustrated in FIG. 3, in step S2, the control module 10 reads the eye data 181 for the three-dimensional model of the eye to be used from the data storage 18. If eye data 181 for a plurality of models of the eye is stored, the user is requested to make a selection in this respect and the latter is accepted.

The control module 10 preferably activates the visualization module 13. On the basis of the selected eye data 181, the visualization module 13 generates the corresponding three-dimensional model of the eye and displays the latter on the display 17 in the user interface 171. The three-dimensional model of the eye comprises a three-dimensional view and/or a plan view and a cross-sectional view of the eye 2. In one variant, the visualization module 13 is configured to display on the display 17 a visualization, which corresponds to the view of the user emerging from viewing windows and/or monitors of the laser device 3 during an actual execution of a selected cut pattern. During the visualization, features defined by the abovementioned measurement data and/or image data are preferably also superposed onto the three-dimensional model of the eye.

Figure 9:
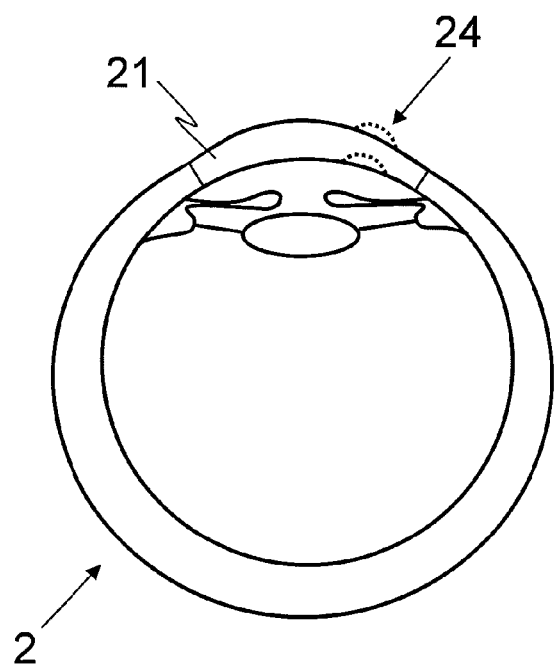
FIG. 9 schematically shows a cross section of an eye with keratoconus.

FIG. 9 shows a cross-sectional view of the eye 2, in which the dashed line schematically illustrates a keratoconus 24 as an example of a pathological thinning and bulging of the cornea 21 (corneal thinning).

Figure 10:
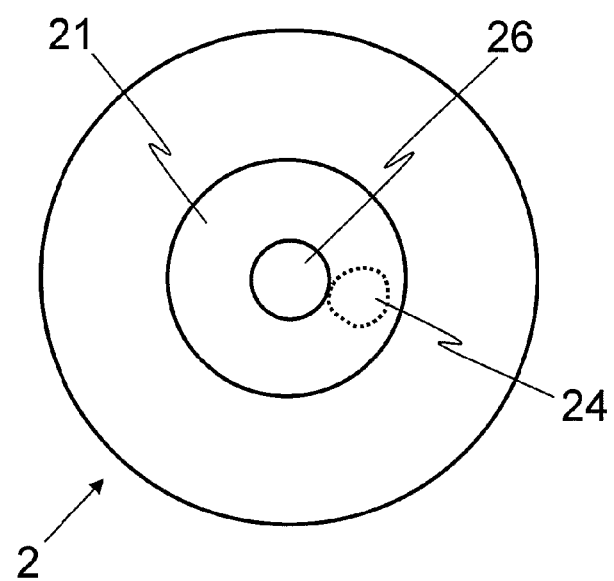
FIG. 10 schematically shows a plan view of an eye with keratoconus.

FIG. 10 shows a plan view of the eye 2, in which the keratoconus 24 is illustrated schematically on the cornea 21 using a dashed line, wherein the keratoconus 24 in the present example partly overlaps the iris 25 and adjoins the pupil 26.

In optional step S3, for example if the user selected and preset a corresponding option, the control module 10 activates the reference generator 113 for automatically generating a target reference in the three-dimensional model of the eye. By way of example, depending on what was preset, the reference generator 113 determines one (or more) geometric reference(s) in the three-dimensional model of the eye, for example a reference point, a reference line, a reference cross and/or a reference grid, based on the optical axis of the laser device 3 or characteristic eye features. In one variant, the reference generator 13 additionally generates construction grids, which are for example imaged on surfaces of eye structures, and/or discretized volumes. Height and width lines, polar and spherical coordinate grids, and also hexagonal grids are listed here as examples. The geometric reference(s) is (are) stored in the data storage and displayed in the three-dimensional model of the eye on the display 17 by means of the visualization module 13.

Figure 11:
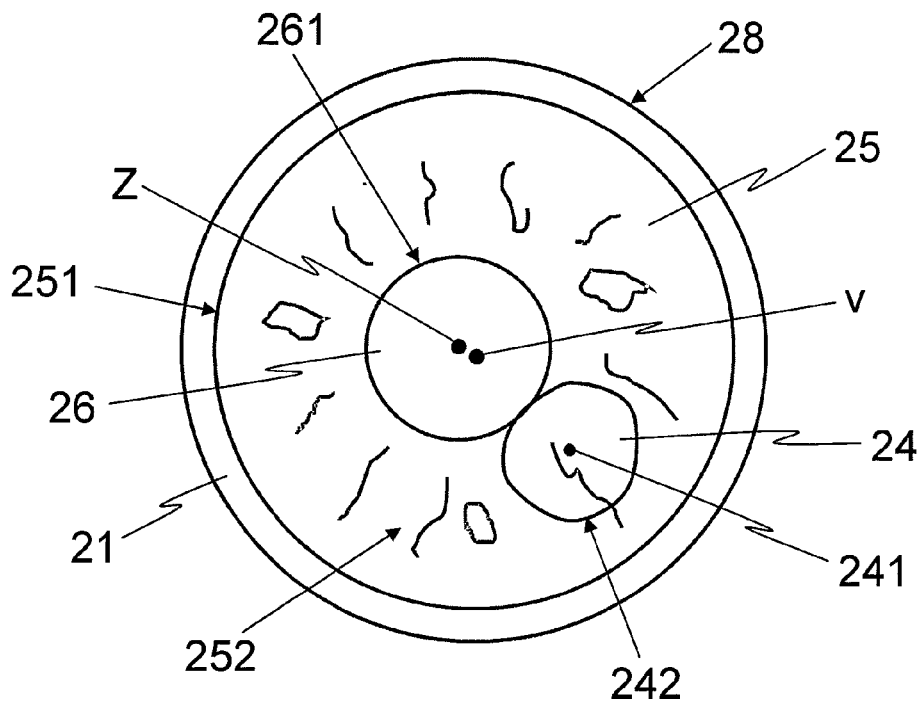
FIG. 11 schematically shows a plan view of an eye with various possible geometric references.

FIG. 11 shows a plan view of the eye, in which the iris 25 is illustrated with the encircling limbus 28. FIG. 11 illustrates various examples of geometric references which are generated by the reference generator 113: the pupil 26, the edge of the pupil 261, the center Z of the pupil 26, the optical or visual axis v, the center of the keratoconus 241, the edge of the keratoconus 242, the limbus 28, the edge of the iris 251 and/or characteristic features of the iris pattern 252. By way of example, the optical or visual axis v is determined by a measurement method, in which the user directs his or her gaze to one or more optical reference markers. Further examples of geometric references comprise the lens 22, the thinnest point on the cornea 21, an inclusion or scar in the cornea 21, the position of implants or vessels in the choroid and structures in the retina 23.

Figure 5:
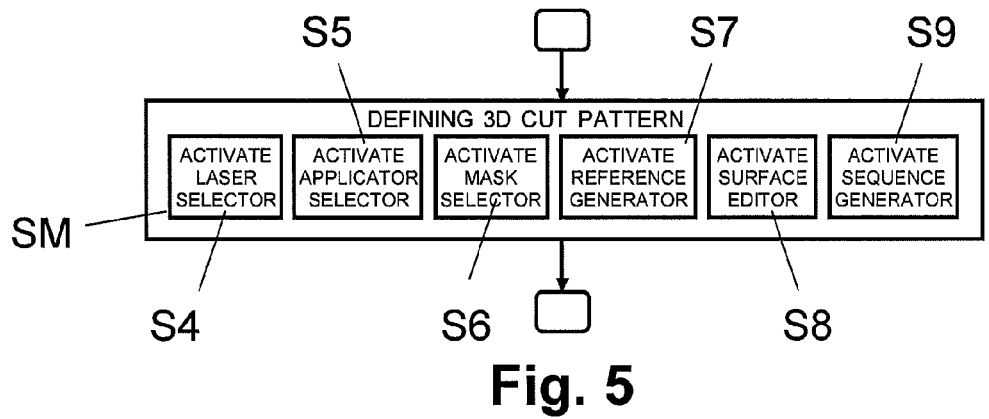
FIG. 5 shows a flowchart which illustrates a possible sequence of steps for defining the three-dimensional cut pattern.

After determining the model of the eye and possibly determining an automatically generated reference, the control module 10 allows the user to define a three-dimensional cut pattern in step SM. To this end, various editing functions are available to the user via the user interface 171; these functions will be described in the following text with reference to FIGS. 5, 6 and 7.

If laser data 182 for a plurality of opthalmological laser devices 3 is stored and/or if the user selects an editing function for selecting and/or changing a particular laser device 3 via the user interface 171, the control module 10 activates the laser selector 101 (see FIG. 5) in step S4. If a plurality of laser devices 3 are defined, the laser selector 101 accepts a selection in this respect by the user. The laser parameters of the selected laser device 3 are displayed to the user on the user interface 171, changes are accepted and the updated laser data 182 is stored in the data storage 18. The laser data 182 can be defined by the user before or during a treatment via the user interface 171, for example according to a request by the user interface 171. In the process, the user is supplied with ranges for the various laser parameters depending on the laser data 182 of the selected laser device 3, and the user can set the values for user-definable laser parameters in said ranges. The laser parameters of the selected laser device 3 and, in particular, the user-defined laser parameters are associated with the cut pattern data 186 or are stored as part of the cut pattern data 186. Additionally, the laser selector 101 determines the shape and dimensions of the projected beam cone 32 on the basis of the current laser data 182 of the selected laser device 3, and said shape and dimensions are stored in the data storage 18 as beam cone data. The visualization module 13 preferably charts, on the display 17, a three-dimensional representation of the beam cone 32 in the user interface 171 in relation to the three-dimensional model of the eye. In one variant, the visualization module 13 also charts, on the display 17, masks, suction rings, and further surgical auxiliary means in relation to the three-dimensional model of the eye.

If the user selects an editing function for selecting, changing and/or positioning an application element 34 via the user interface 171, the control module 10 activates the applicator selector 112 in step S5. The applicator selector 112 shows the user the available application elements 34 on the user interface 171 and accepts a selection in this respect. The selection of the application element 34 is stored in the data storage 18 and illustrated on the display 17 in a non-applied state by the visualization module 13. The applicator selector 112 is additionally designed to accept instructions by the user via the input elements 16 for the relative positioning of the selected application element 34 in relation to the three-dimensional model of the eye, i.e. for the virtual application on the eye 2. If the positioning of the application element 34 corresponds to contacting and deforming the eye 2, the deformation module 12 is activated. On the basis of the current eye data 181 of the selected model of the eye, the selected application element 34 and the relative position thereof in relation to the eye 2 or the model of the eye, the deformation module 12 determines a deformed three-dimensional model of the eye which represents the eye 2 in the state with the attached application element 34. The visualization module 13 displays, on the display 17, the deformed three-dimensional model of the eye with the applied application element 34. Hence, the user interface allows the user to select and position application elements 34 in a flexible fashion on an eye 2 in the virtual space visualized by graphics.

Figure 8:
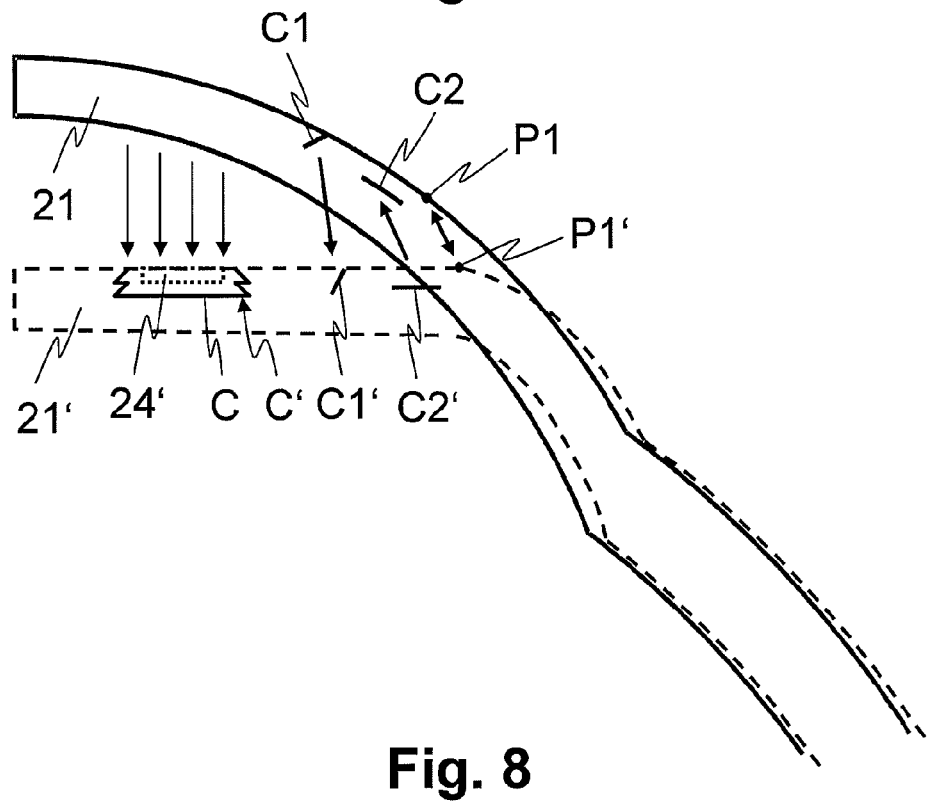
FIG. 8 schematically shows, in a cross section, a section of a cornea in a non-deformed state and in a deformed state as a result of applanation.

FIG. 8 schematically shows a section of an example of a deformation of the cornea 21 by applanation in a cross-sectional view. Here, reference sign 21' relates to the cornea in the deformed state, illustrated by the dashed line.

If the user selects an editing function for selecting, changing and/or positioning a projection mask 33 via the user interface 171, the control module 10 activates the mask selector 111 in step S6. The mask selector 111 shows the user the available projection masks 33 on the user interface 171 and accepts a selection in this respect. The selection of the projection mask 33 is stored in the data storage 18 and displayed on the display 17 by the visualization module 13. The mask selector 111 is additionally designed to accept instructions by the user via the input elements 16 for the relative positioning of the selected projection mask 33 in relation to the three-dimensional model of the eye, i.e. for the virtual positioning in front of the eye 2. In one option, the projection mask 33 is automatically attached to a selected application element 34. In an embodiment variant, the mask selector 111 additionally allows the user to change the dimensions and/or transmission parameters of the opaque or light-damping mask regions 33' and store the latter as a changed projection mask 33 in the data storage 18. The visualization module 13 displays, on the display 17, the three-dimensional model of the eye with the positioned and possibly changed projection mask 33. Thus, the user interface allows the user to flexibly select, position, and change projection masks 33 in the virtual space visualized by graphics. Moreover, the mask selector projection mask cone 32 defined to say whether laser pulses is 111 checks whether the selected 33 results in shadowing of the beam by the stored beam cone data, that is radiation of the femtosecond or shadowed by the projection focused covered mask 33. If mask-dependent shadowing is detected, the mask selector 111 shows this to the user via the user interface 171 and, in step S6, awaits the selection of an alternative projection mask 33 or a correction of the mask regions 33'. In an embodiment variant, the mask selector 111 automatically generates (e.g. following an appropriate user instruction) a corrected projection mask 33, which does not effect shadowing and illustrates the latter to the user on the user interface 171.

Figure 19:
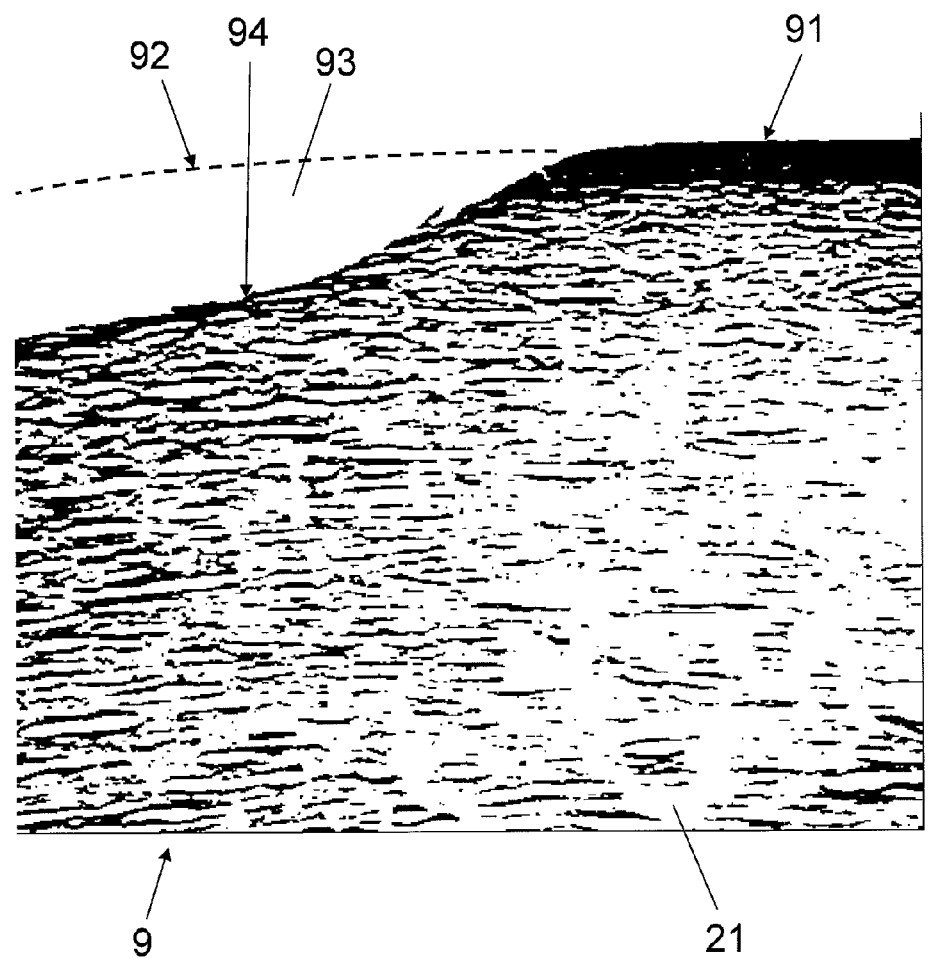
FIG. 19 shows a cross-sectional image through a segment of the cornea in the non-deformed state after a corneal flap was cut in the deformed state.

Following FIG. 8, FIG. 19 shows a cross-sectional image of an example of a corneal segment 9 in the non-deformed state after a corneal flap 93 was generated by a planar cut surface in the deformed state. The original surface of the cornea 21 delimited by the epithelium 91 is illustrated in FIG. 19 by the dashed line denoted by reference sign 92. The example illustrates the influence of the deformation on the cut result: the cut surface 94, which was straight in the deformed state, is curved in the non-deformed state.

If the user selects an editing function for (manually) defining and/or changing a geometric reference via the user interface 171, the control module 10 activates the reference generator 113 in step S7. The reference generator 113 shows the user various available types of geometric references on the user interface 171 and accepts a selection in this respect. A selected type of reference is illustrated on the display 17 by the visualization module 13. As already mentioned previously, certain types of references are automatically generated by the reference generator 113 and are positioned in the original or deformed model of the eye. However, geometric references can also be defined manually by the user via the user interface 171 and be positioned in the non-deformed or deformed model of the eye, for example by entering position coordinates or by displacing an illustration of the reference by means of the positioning elements. Moreover, geometric references can also be defined by a (visualized) superposition of the model of the eye with external measurement data and/or image data, which for example define the major curve axis in the case of astigmatism, the thinnest measured point of the cornea 21, an inclusion or a scar in the cornea 21 or implants. A defined geometric reference, associated with the relevant eye data 181, is stored in the data storage 18 and displayed on the display 17 by the visualization module 13 in the non-deformed or deformed three-dimensional model of the eye. Thus, the user is flexibly able to define geometric references in the (non-deformed and/or deformed) three-dimensional model of the eye via the user interface.

Figure 12:
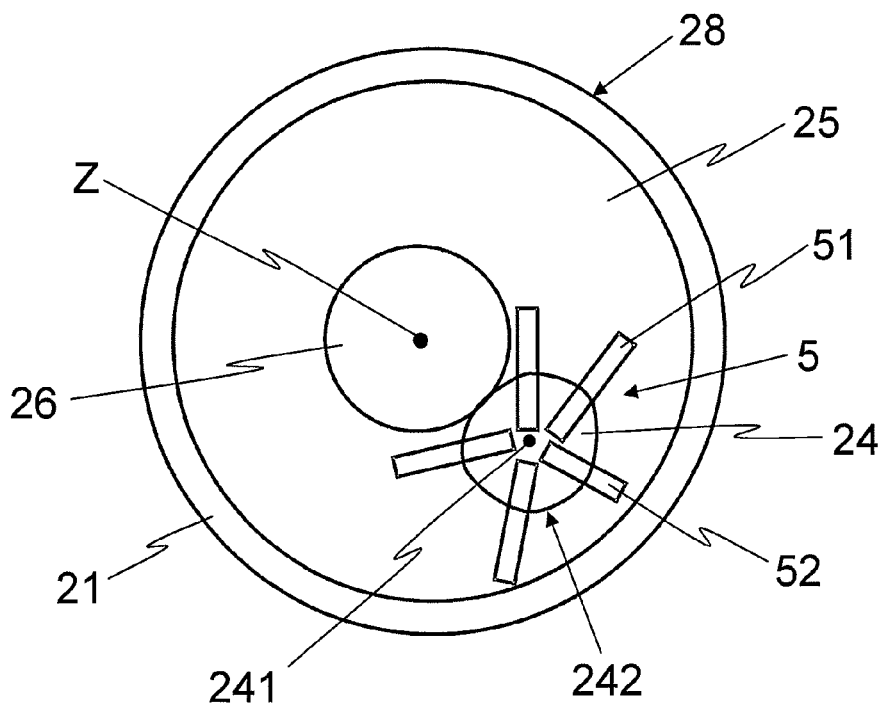
FIG. 12 schematically shows a plan view of an eye with certain geometric references and a cut pattern for supporting the keratoconus.

FIG. 12 shows a plan view of the eye, in which the iris 25 is illustrated with an encircling limbus 28. FIG. 12 schematically illustrates an example in which the center Z of the pupil 26 and the center of the keratoconus 241 were selected as geometric references. Compared to FIG. 11, FIG. 12 shows that the visualization module 13 reduces the (three-dimensional) illustration of the model of the eye to the selected geometric references and filters other possible geometric references such as the optical/visual axis v or iris pattern 27, and so the user has a better overview of the illustration.

If the user selects an editing function for defining, changing and/or positioning a cut via the user interface 171, the control module 10 activates the cut surface editor 114 in step S8. The cut surface editor 114 enables the user to define cuts according to various cut classes: cuts with a cut surface defined as a second order surface, cuts with a cut surface defined as a spline surface, cuts with a cut surface defined by a cutting line and cutting line trajectory and cuts with a cut surface defined by a stored three-dimensional cut pattern.

Figure 6:
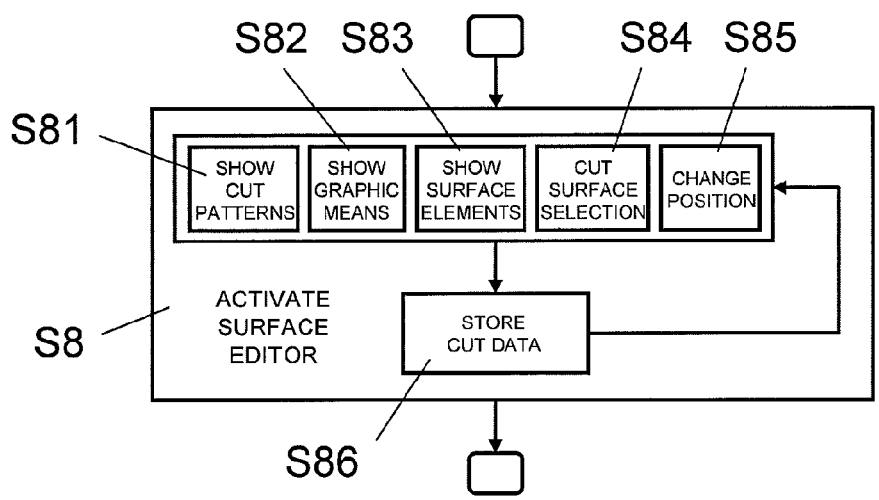
FIG. 6 shows a flowchart which illustrates a possible sequence of steps for defining steps according to different cut classes.

In the following text, the functions of the cut surface editor 114 are described in more detail with reference to FIG. 6.

If the user selects the editing function for defining a cut with a cut surface defined by a stored three-dimensional cut pattern, the cut surface editor 114 shows to the user on the user interface 171 in step S81 the available cut patterns defined by the cut pattern data 185 and said editor accepts a selection in this respect. The cut surface defined by the selected cut pattern is displayed, in the three-dimensional model of the eye, on the display 17 by the visualization module 13, with the positioning and orientation of the selected cut pattern in relation to the defined (preferred or assigned) geometric reference of the model of the eye being implemented in the process. If the selected cut pattern is intended to be edited beyond the definition of cut surfaces (e.g. deleting or adding a cut surface, or changing a geometric reference, execution sequence, application element, projection mask and/or beam cone), the additional functions of the cut pattern editor 11 relating thereto are activated. In an embodiment variant, the cut surface editor 114 activates the cut recorder 115 in step S81; the latter is configured to generate, based on user instructions, a virtual tissue cut in the visualized three-dimensional model of the eye by moving the beam cone 32 defined by the beam cone data. The virtual tissue cut is stored as a three-dimensional cut pattern in the data storage 18 and displayed on the display 17 by the visualization module 13.

FIG. 12 schematically illustrates in a plan view a cut pattern 5 for correcting a keratoconus 24. The cut pattern 5 comprises a plurality of pockets 51, 52 cut into the cornea 21, which are respectively generated by a separate cut surface. The pockets 51, 52 are cut for inserting a stabilizing material, e.g. by injecting riboflavin (vitamin B2), which polymerizes in UV light. The cut pattern data 186 of the cut pattern 5 preferably comprises a function indication, here, e.g., supporting a keratoconus 24 by means of a polymerizing liquid, which function indication determines a geometric reference of the model of the eye preferably utilized for the positioning and orientation of the cut pattern 5, in this case, for example, the center of the keratoconus 241 or the edge of the keratoconus 242. The cut pattern editor 11 or the cut surface editor 114 positions the cut pattern 5 in relation to the preferred or assigned geometric reference (default positioning).

FIGS. 13, 14, 15, 16 and 17 illustrate further examples of cut patterns or defined cut surfaces in a plan view of the cornea 21.

Figures 13, 14:
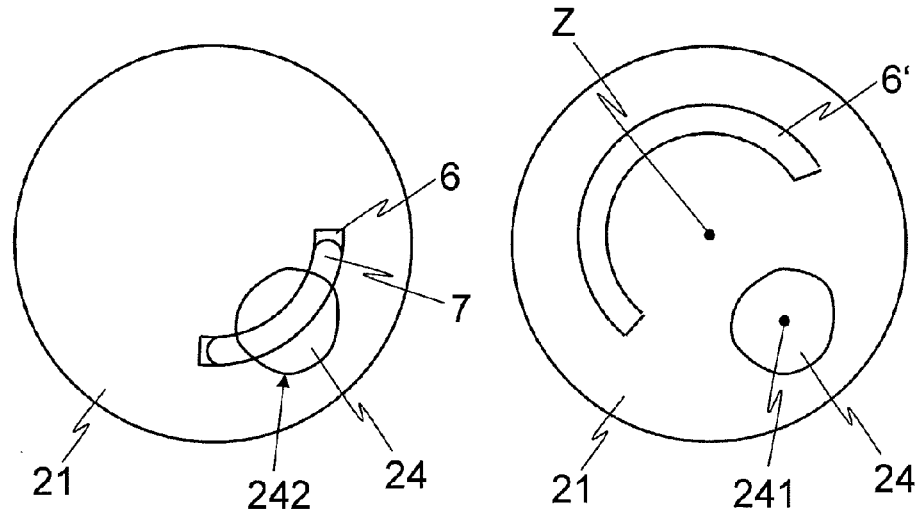
FIG. 13 schematically shows a plan view of a cornea with a cut pattern for supporting the keratoconus by means of a mechanical support insert.
FIG. 14 schematically shows a plan view of a cornea with a cut pattern to pull flat the bulge in the cornea produced by the keratoconus.

FIG. 13 illustrates a cut pattern, or a pocket 6 cut into the cornea 21 and determined by a defined cut surface, for supporting the keratoconus 24 by means of an implant 7 (mechanical support insert) which is inserted into the cut pocket 6, e.g. a so-called Intac made of plastics. In the example of FIG. 13, the edge of the keratoconus 242 is assigned as preferred (default) geometric reference for this cut pattern or this cut surface. The cut pattern, or the pocket 6 determined by the defined cut surface, is preferably arranged centered with the edge of the keratoconus 242, with the curvature of the pocket 6 for example being defined by an arc about the center Z of the pupil.

FIG. 14 illustrates a cut pattern, or a pocket 6' cut into the cornea 21 and determined by a defined cut surface, for flattening by pulling the bulge in the cornea 21 produced by the keratoconus 24 by means of an implant (not illustrated) which is inserted into the pocket 6' produced by the cut surface. In the example in FIG. 14, the center Z of the pupil and the center of the keratoconus 241 are assigned as preferred (default) geometric references for this cut pattern or this cut surface. The cut pattern, or the pocket 6' determined by the defined cut surface, is preferably arranged on the side of the center Z of the pupil situated opposite to the center of the keratoconus 241, with the curvature of the pocket 6' for example being defined by an arc about the center Z of the pupil.

Figures 15, 16:
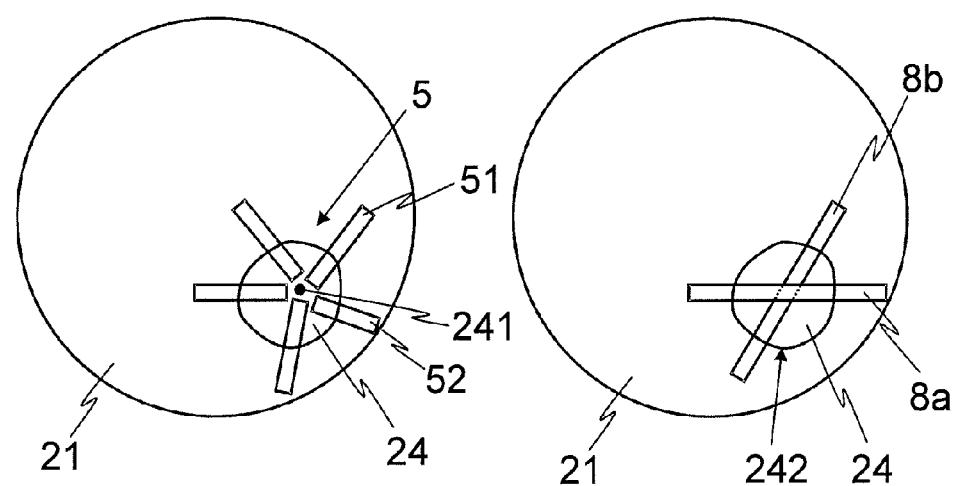
FIG. 15 schematically shows a plan view of a cornea with a cut pattern for supporting the keratoconus.
FIG. 16 schematically shows a plan view of a cornea with a cut pattern for supporting the keratoconus by means of two mutually crossing support inserts.

FIG. 15 illustrates the cut pattern 5 for correcting the keratoconus 24 comprising a plurality of pockets 51, 52 cut into cornea 21 and described above with reference to FIG. 12. In the example shown in FIG. 15, the center of the keratoconus 241 is assigned as preferred (default) geometric reference for this cut pattern. The cut pattern, or the pockets 51, 52 determined by the defined cut surfaces, is preferably arranged in a star-like fashion with respect to the center of the keratoconus 241, wherein the punctures or openings of the pockets 51, 52 are respectively attached to the side of the pockets 51, 52 facing away from the center of the keratoconus 241.

FIG. 16 illustrates a cut pattern with two pockets 8a, 8b, respectively determined by a defined cut surface, which are cut into the cornea 21, crossed and spaced apart while lying above one another, for supporting the keratoconus 24 by means of mechanical support inserts, which are inserted into the cut pockets 8a, 8b. In the example in FIG. 16, the edge of the keratoconus 242 is assigned as preferred (default) geometric reference for this cut pattern or these cut surfaces. The cut pattern, or the cross-shape defined by the cut surfaces, is preferably arranged centered with the edge of the keratoconus 242.

Figure 17:
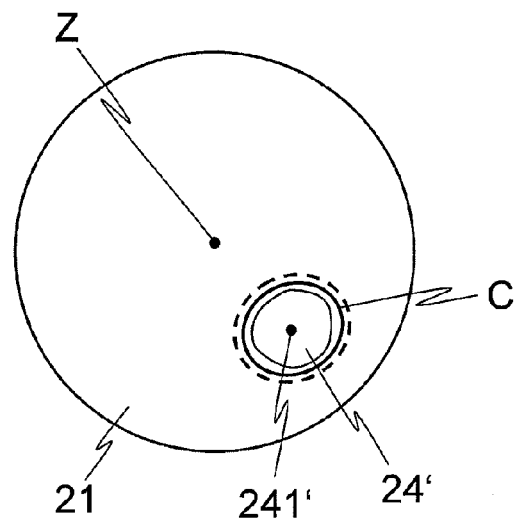
FIG. 17 schematically shows a plan view of a cornea with a cut pattern for local keratoplasty.

FIG. 17 schematically illustrates a cut pattern C for local keratoplasty in a plan view. In a conventional corneal transplant, a significant part of the cornea 21 (for example >50% of the cornea) is replaced by a corneal disk centrally cut out of a donor cornea. In contrast thereto, in the local keratoplasty illustrated in FIG. 17, an injured or damaged piece of cornea 24', e.g. a local corneal caustic burn or inclusions/damage in the cornea 21, is replaced locally about the damaged point in a tailored fashion. FIG. 8 illustrates the cut pattern C for the local keratoplasty in a cross section. FIG. 8 shows that the cut pattern C is dimensioned and arranged such that it completely comprises the damaged piece of cornea 24'. The cut pattern C comprises a plurality of cut surfaces cut into the cornea 21, which cut surfaces define a (cut-out) cylinder in which the encircling edge region C' has a profile for an interlocking hold of an appropriately shaped corneal replacement part, and this affords a better hold of the replacement part in the cornea of the patient. The profile of the edge region C' is for example serrated or tiered in a saw-tooth fashion. The cut pattern data 186 of the cut pattern C preferably comprises a function indication, here, e.g., local keratoplasty, which function indication determines a geometric reference of the model of the eye preferably utilized for the positioning and orientation of the cut pattern C, in this case, for example, the center 241' of the damaged corneal piece 24'. In order to avoid sequence-based shadowing, the lower cut surfaces of the cut pattern C facing away from the corneal surface are cut before the upper cut surfaces of the cut pattern C facing the corneal surface in the local keratoplasty. Additionally, it should also be noted here that the computer system 1 and the laser device 3 connected thereto can be used not only for producing and processing cut patterns on patient eyes, but are suitable and also can be used, in particular, for producing replacement corneal pieces from donor corneas or implants. An advantage of the local keratoplasty in particular is also that a donor cornea can be used for the production of a plurality of replacement corneal pieces for one or more patients.

If the user selects the editing function for defining a cut with a cut surface defined by a cutting line and a cutting line trajectory, the cut surface editor 114 shows to the user on the user interface 171 in step S82 graphical auxiliary means for defining a cutting line in the visualized three-dimensional model of the eye, for example individual or a plurality of straight line segments between respectively two user-defined points, or a curved line through a plurality of user-defined points, wherein the points are in each case defined by a three-dimensional position in the three-dimensional model of the eye. However, the individual points are preferably defined by the user on a surface in the visualized three-dimensional model of the eye, for example on the cornea 21, on the lens 22, on the retina 23 or on a defined meridian cut through the eye tissue. The defined cutting line is displayed on the display 17 in the three-dimensional model of the eye by the visualization module 13. The cut surface editor 114 is additionally designed to accept instructions by the user via the input elements 16 for defining a cutting line trajectory in the three-dimensional model of the eye and for changing the cutting line. The cutting line trajectory specifies the direction in which the defined cutting line is intended to be moved (e.g. displaced or rotated) in the three-dimensional model of the eye for executing the cut and therefore defines a cut surface based on the cutting line.

If the user selects the editing function for defining a cut with a cut surface defined as a surface of second order or as a spline surface, the cut surface editor 114 shows to the user on the user interface 171 in step S83 the available surface elements of second order, defined by the surface element data 185, and accepts a selection in this respect. The selected surface element is displayed on the display 17 by the visualization module 13. The cut surface editor 114 additionally allows the user automatically to define cut surfaces, which are equidistant from a particular surface, for example in relation to selected eye structures and/or application elements.

If the user selects an editing function for changing a cut surface via the user interface 171, the cut surface editor 114 accepts instructions from the user via the input elements 16 in step S84 for changing a selected cut surface in the three-dimensional model of the eye. In particular, in order to change a cut surface, the cut surface editor 114 allows the user to scale the size of a selected surface element or cutting line, or a cut pattern, to delimit the cut surface along one or more boundary lines, to change the curvature of the cut surface, to change the orientation of the cut surface and/or to define or change the cut direction of the cut surface. For a cut surface, the cut direction determines the direction in which the pulse grid of the femtosecond laser pulses is built up. By way of example, in the case of a cylindrical cut, the pulse grid can be defined such that the cut is executed e.g. helically, from the bottom to the top, or that, as in the case of a jigsaw or a knife, vertical cuts executed from the bottom to the top are respectively driven one after another in a circle. This example shows the flexibility afforded by the femtosecond laser technology, in which shadowing conditions and cutting time in these cutting guides can be optimized very differently and by means of the computer system, as will be described below. In one variant, it is also possible for a start point (initial point) for the pulse grid of the femtosecond laser pulses also to be defined, e.g. by selecting one of a plurality of start point options defined for the relevant cut surface, in addition to the cut direction of a cut surface.

If the user selects an editing function for positioning a cut surface in the (non-deformed and/or deformed) three-dimensional model of the eye via the user interface 171, the cut surface editor 114 accepts instructions from the user via the input elements 16 in step S85 for changing the relative position in relation to the geometric reference. By way of example, the relative position is defined by inserting coordinates, or preferably by using the positioning elements through graphical displacement of the relevant cut surface, in the (non-deformed or deformed) three-dimensional model of the eye. By way of example, in addition to entering x/y coordinates by means of a computer mouse, a touchpad or a trackball, z coordinates can be defined by means of an additional operating element, e.g. a scroll wheel. The positioning is effected directly in a three-dimensional graphical illustration and/or in a combined illustration of a plan view and a cross-sectional view of the three-dimensional model of the eye (to this end, see also the subsequent discussions in relation to FIG. 8).

If the user indicates to the surface cut editor 114 via the user interface 171 that the defining, changing and/or positioning of the cut is complete, the surface cut editor 114 in step S86 stores the corresponding cut data in the data storage 18.

Here, it should be noted that the control module 10 allows a user to define and to position cuts using the surface cut editor 114 before an application element 34 is selected and positioned by means of the applicator selector 112. The deformation module 12 is configured to determine, based on the three-dimensional cut pattern determined by the defined cuts and the selected and positioned application element 34, a deformed three-dimensional cut pattern, in which the cut surfaces positioned in the three-dimensional model of the eye are correspondingly also deformed into a deformed state together with the deformation of the model of the eye and so points of the deformed cut surfaces are in each case defined by a transformed point of the deformed model of the eye, which transformed point is based on the originally common point of the non-deformed model of the eye and the non-deformed cut surface. Therefore, the user can define cut surfaces in the non-deformed state of the virtual eye and can automatically let them be transformed into a deformed state of the eye by virtual application of the application element 34.

FIG. 8 shows a cross section of a portion of the non-deformed cornea 21 and the deformed cornea 21' and cutting lines C1, C2, C1', C2' (or cut surfaces) and cut points P1, P1' positioned therein. As illustrated schematically in FIG. 8, the cutting line C1 is positioned in the non-deformed state of the cornea 21 and transformed into the cutting line C1' in the deformed state of the cornea 21' when the cornea 21 deforms (by means of the deformation module 12).

Conversely, the cutting line C2' is positioned in the deformed state of the cornea 21' and transformed into the cutting line C2 in the non-deformed state of the cornea 21 when undoing the deformation (by means of the deformation module 12). An individual cut point P1, P1' is also correspondingly transformed from a position in the non-deformed state of the cornea 21 into a position in the deformed state of the cornea 21', or reverse transformed therefrom, by a deformation or by undoing the deformation (by means of the deformation module 12). As a result of the deformation or reverse transformation, straight lines are in general twisted, extended/compressed and bent (see also FIG. 19).

If a plurality of steps were defined for a three-dimensional cut pattern, the control module 10 enables the editing function for defining an execution sequence for the user. If the user selects the editing function for defining the execution sequence via the user interface 171, the control module 10 activates the sequence generator 116 in step S9. In an embodiment variant, the sequence generator 116 is activated automatically in step S10 by the cut pattern generator 117.

Figure 7:
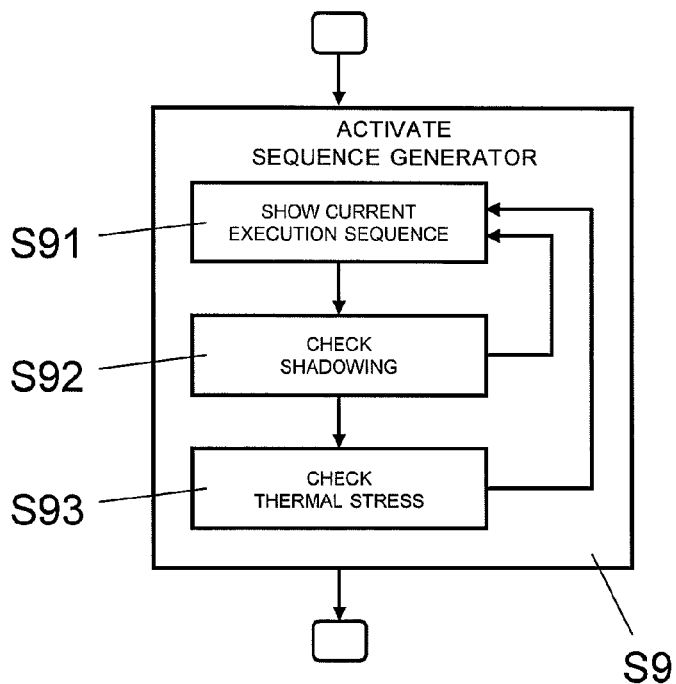
FIG. 7 shows a flowchart, which illustrates a possible sequence of steps for defining and checking an execution sequence of individual steps of a cut pattern.

In the following text, the functions of the sequence generator 116 are described in more detail with reference to FIG. 7.

In step S91, the sequence generator 116 shows the user the current execution sequence of the defined steps on the user interface 171. In the process, an initial execution sequence is defined without user instructions and it corresponds to the (temporal) sequence in which these steps were defined. The sequence generator 116 accepts instructions by the user via the user interface 171 for changing and/or applying the current or changed execution sequence. The user can also place stop points for the simulation and/or the actual treatment and store these with the cut pattern data 186. The stop points allow the user to undertake changes to the cut pattern data and, in particular, to the (user-definable) laser parameters, for example during a simulation and/or actual treatment.

The sequence generator 116 carries out a plausibility check in steps S92 and S93 for the execution sequence defined in step S91. In a variant, the plausibility check also comprises the detection of penetrating cuts, which penetrate eye structures, for example the surface of the cornea 21 or the lens 22. A warning for detected penetrating cuts is displayed to the user on the user interface 171 in each case.

In step S92, the sequence generator 116 checks whether the execution of the cuts according to the defined execution sequence results in shadowing of cuts to be executed later by cuts to be executed earlier, that is to say whether focused radiation of the femtosecond laser pulses for generating the cut surface to be generated later is covered or shadowed by the cut to be generated earlier. In order to determine the covering or shadowing, an investigation is carried out as to whether the beam cone 32 defined by the stored beam cone data is interrupted by a cut generated earlier when executing a later cut. If sequence-dependent shadowing is detected, the sequence generator 116 shows this to the user on the user interface 171 and expects a correction of the execution sequence in step S91. In an embodiment variant, the sequence generator 116 automatically generates a corrected execution sequence (for example following a corresponding user instruction) which affords no shadowing and displays said execution sequence to the user on the user interface 171.

In an embodiment variant, the sequence generator 116 additionally automatically separates overlapping cut surfaces into separate cut surfaces, which are then treated as separate cut surfaces in the execution sequence.

In a further embodiment variant, the sequence generator 116 takes into account the resorption of gas in the tissue produced during the breakdown of tissue as a result of the laser treatment when determining the sequence-dependent shadowing or when generating a corrected execution sequence. In the process, stored resorption times are used which specify the time for re-attaining transparency in the tissue after the treatment thereof. After the resorption, an executed cut does not cause impeding shadowing and cuts can be executed again in the tissue lying therebelow.

In an additional embodiment variant, the sequence generator 116 moreover takes into account and/or changes the cut direction of the cut surfaces, i.e. the direction in which the pulse grid of the femtosecond laser pulses is built up, when determining the sequence-dependent shadowing or when generating a corrected execution sequence. By way of example, an optimization is carried out in the process, in which the execution sequence, cut direction and/or start point of the cut surfaces of the cut pattern defined by the user are adapted such that the steps are carried out as quickly as possible and without shadowing. In general, both the sequence of cut surfaces and the pulse grid within a cut surface are executed from the bottom to the top, with the scan direction with the highest feed velocity being given priority.

If a shadowing-free execution sequence is present, the sequence generator 116 checks in optional step S93 whether an expected thermal stress on the eye 2 exceeds a defined boundary value when executing the cuts according to the defined execution sequence. In the process, the expected thermal stress on the eye 2 is determined as described in, for example, EP1810647, where a modeling module determines the (thermal) stress on the eye structures resulting from the treatment by the laser beam, based on the model of the eye and the light propagation in the eye and the defined laser parameters, taking into account absorption coefficients which are assigned to the eye structures. According to EP1810647, tissue damage outside of a cut is substantially avoided by reducing the mean irradiance in the cut region (processing area) and by reducing the maximum temperature in the tissue outside of the cut so that stress limits of eye structures are not exceeded. If a sequence-dependent thermal overload is detected, the sequence generator 116 shows this to the user on the user interface 171 and expects a correction of the execution sequence in step S91. In an embodiment variant, the sequence generator 116 automatically generates a corrected execution sequence (e.g. following a corresponding user instruction) which does not cause thermal overload and displays this to the user on the user interface 171. If an execution sequence without an expected overload is present, the sequence generator 116 stores the defined execution sequence.

If the user indicates to the control module 10 via the user interface 171 that the definition of the three-dimensional cut pattern in step SM has been completed, the cut pattern generator 117 generates a three-dimensional cut pattern based thereon in step S10. The three-dimensional cut pattern basically defines one or more tissue cuts through one or more cut surfaces positioned in relation to at least one geometric reference in the non-deformed or deformed model of the eye, which cut surfaces have an execution sequence assigned thereto or are ordered according to the execution sequence. The cut surfaces are defined in the three-dimensional cut pattern in the form of e.g. macroinstructions. In an alternative, or additionally, the three-dimensional cut pattern comprises pulse grid instructions for controlling the laser device 3 for each cut surface. Along with the cut pattern data of a defined cut pattern, the (manually or automatically) defined geometric references are also transferred to the laser device 3.

If the user selects a simulation function for simulating the generated cut pattern via the user interface 171, the control module 10 activates the cut simulator 14 in step S11; otherwise, the cut pattern data 186 of the three-dimensional cut pattern is stored in the data storage 18 in step S12.

The cut pattern data 186 can additionally be transferred to an Internet-based web server as cut pattern files via a telecommunication network by means of the communication module 19, and can be stored on said server in order to be reused.

The cut simulator 14 is configured to simulate the execution of the tissue cuts defined by the three-dimensional cut pattern and to visualize this on the display 17. In doing so, the three-dimensional cut pattern is preferably executed in a step-by-step mode, wherein an instruction for continuing the simulation with the next step, or instructions for selecting and executing the various editing functions (step SM) for changing the three-dimensional cut pattern or cuts contained therein, is/are accepted from the user after each step. In the process, depending on the selected simulation mode, the execution of a cut surface, a cut surface component or a defined number of femtosecond laser pulses is simulated and visualized in a single step. In an embodiment variant, the user can additionally also place stop points for the simulation and/or the actual treatment, e.g. before or after executing a certain cut surface or cut surface component, or after executing a defined number of femtosecond laser pulses. The three-dimensional cut pattern can also be changed in the simulation mode (and, in one variant, even during the actual treatment) at a stop point, for example, by the functions of the cut pattern editor 11. The three-dimensional cut pattern can be changed in particular by the following operations: repositioning of a cut surface, reorientation of a cut surface, changing a cut direction of a cut surface, deleting a cut surface, deleting a cut surface component, changing a cut surface, adding a cut surface, duplicating a cut surface, changing a geometric reference, changing an execution sequence for the cut surfaces, changing an application element to be attached to the eye when executing the tissue cuts, changing a projection mask to be positioned in front of the eye when executing the tissue cuts and/or changing a beam cone 32 defined by focused radiation of the femtosecond laser pulses. Moreover, the cut pattern can be changed as a whole, for example by scaling (changing the size), (re-)orientation and/or repositioning displacing).

Finally, it should be noted that although a computer program code was assigned to specific functional modules in the description and that the steps were illustrated as being executed in a certain order, a person skilled in the art would however understand that the computer program code can have a different structure and the order of at least certain steps can be changed without deviating from the subject matter for which protection is sought.

What is claimed is:

1. A computer-aided system for generating a three-dimensional cut pattern which defines one or more tissue cuts to be executed in a human eye by means of femtosecond laser pulses, comprising:
    a data storage with eye data which defines a three-dimensional model of the eye;
    a visualization module configured to generate and display the three dimensional model of the eye in a user interface;
    a reference generator which is configured to define and to store at least one geometric reference in relation to the three-dimensional model of the eye; the visualization module further configured to display the at least one geometric reference in the three-dimensional model of the eye in the user interface;
    a cut surface editor which is configured to define via the user interface, based on user instructions, a cut surface and to position the cut surface in the three-dimensional model of the eye displayed in the user interface in relation to the at least one geometric reference, based on user instructions for defining orientation and a three-dimensional position of the cut surface in the three-dimensional model of the eye, the three-dimensional position of the cut surface being defined by the user using positioning elements of the computer to displace the cut surface in the three-dimensional model of the eye, and to repeat defining and positioning of cut surfaces based on user instructions, until the user indicates via the user interface that defining and positioning of a cut is complete and a plurality of cut surfaces have been defined and positioned by the user via the user interface in the three-dimensional model of the eye; and
    a cut pattern generator which is configured to generate the three-dimensional cut pattern for defining tissue cuts based on the plurality of cut surfaces defined and positioned by the user via the user interface in the three-dimensional model of the eye, and to store for the three-dimensional cut pattern cut pattern data for controlling an ophthalmological laser device; and
    a sequence generator which is configured to determine an execution sequence for the plurality of cut surfaces defined and positioned by the user via the user interface in the three-dimensional model of the eye, whereby a cut surface which, according to the execution sequence, is to be generated earlier, by a plurality of femtosecond laser pulses, is prevented from covering or shadowing focused radiation of the femtosecond laser pulses for generating a cut surface which, according to the execution sequence, is to be generated later, and wherein the sequence generator determines the covering or shadowing on the basis of a beam cone defined by focused projection of the femtosecond laser pulses, by checking whether the beam cone for generating a cut surface which, according to the execution sequence, is to be generated later, is interrupted by a cut surface which, according to the execution sequence, is to be generated earlier.

2. The system of claim 1, wherein the cut surface editor is configured to define the at least one cut surface on the basis of a user-defined cutting line and a user-defined cutting line trajectory.

3. The system of claim 1, wherein the cut surface editor is configured to define the at least one cut surface on the basis of at least one surface element, which can be selected from a list of a plurality of different surface elements on the basis of user instructions.

4. The system of claim 1, further comprising an applicator selector which is configured to determine, based on user instructions, an application element which should be applied to the eye when executing the tissue cuts.

5. The system of claim 1, wherein the sequence generator is configured to determine the execution sequence for the cut surfaces such that an expected thermal stress on the eye does not exceed a defined threshold.

6. The system of claim 1, further comprising a mask selector which is configured to determine, based on user instructions, a projection mask to be positioned in front of the eye when executing the tissue cuts, and to check, based on the determined projection mask and a beam cone defined by focused radiation of the femtosecond laser pulses, whether the cut surfaces of the tissue cuts defined in the three-dimensional cut pattern can be generated without shadowing by the projection mask.

7. The system of claim 1, wherein the visualization module is configured to show on a display, based on the eye data, a visualization of the eye and a beam cone, defined by focused radiation of the femtosecond laser pulses; and a cut recorder which is configured to generate, based on user instructions, a virtual tissue cut in the visualized eye by moving the beam cone, and to store the virtual tissue cut as a three-dimensional cut pattern.

8. The system of claim 1, further comprising a cut simulator which is configured to simulate, based on the eye data and the stored three-dimensional cut pattern, execution of the tissue cuts defined by the three-dimensional cut pattern, and to visualize it on a display; and a cut pattern editor which is configured to adapt, based on user instructions, the stored three-dimensional cut pattern using at least one operation from the following list: repositioning a cut surface, reorienting a cut surface, changing a cut direction of a cut surface, deleting a cut surface, deleting a cut surface component, changing a cut surface, adding a cut surface, duplicating a cut surface, changing a geometric reference, changing an execution sequence for the cut surfaces, changing an application element to be attached to the eye when executing the tissue cuts, changing a projection mask to be positioned in front of the eye when executing the tissue cuts and changing a beam cone defined by focused radiation of the femtosecond laser pulses.

9. The system of claim 1, wherein the cut pattern generator is configured to define tissue cuts in the three-dimensional cut pattern by one or more cut surfaces positioned in relation to a geometric reference, wherein a cut surface is in each case defined by at least one parameter from the following list: cutting line, cutting line trajectory, direction of cut, surface element class, surface element dimensions, surface element curvature and surface element orientation, and wherein an execution sequence is assigned to the cut surfaces.

10. The system of claim 1, wherein the cut pattern generator is configured to define the cut surfaces in the three-dimensional cut pattern in the form of macroinstructions.

11. The system of claim 1, wherein the cut surface editor is configured to adapt, based on user instructions, the at least one cut surface using at least one operation from the following list: scaling the size of the cut surface, delimiting the cut surface along one or more boundary lines, changing a curvature of the cut surface, changing an orientation of the cut surface, changing a cut direction of the cut surface and changing a cut class of the cut surface, wherein the cut class is defined by at least one element of the following list of cut classes: cuts with a cut surface defined as a second order surface, cuts with a cut surface defined as a spline surface, cuts with a cut surface defined by a cutting line and cut direction and cuts with a cut surface defined by a stored three-dimensional cut pattern.

12. A computer-implemented method of generating a three-dimensional cut pattern which defines one or more tissue cuts to be executed in a human eye by means of femtosecond laser pulses, the method comprising:

storing in a computer eye data which defines a three-dimensional model of the eye;

displaying the three-dimensional model of the eye in a user interface;

defining and storing in the computer at least one geometric reference in relation to the three-dimensional model of the eye;

displaying the at least one geometric reference in the three-dimensional model of the eye in the user interface;

defining in the computer, based on user instructions received via the user interface, a plurality of cut surfaces and positioning the plurality of cut surfaces in the three-dimensional model of the eye displayed in the user interface in relation to the at least one geometric reference based on user instructions for defining orientation and a three-dimensional position of the cut surface in the three-dimensional model of the eye, the three-dimensional position of the cut surface being defined by the user using positioning elements of the computer to displace the cut surface in the three-dimensional model of the eye;

repeating the defining and the positioning of cut surfaces based on user instructions, until the user indicates via the user interface that defining and positioning of a cut is complete and a plurality of cut surfaces have been defined and positioned by the user via the user interface in the three-dimensional model of the eye;

generating in the computer the three-dimensional cut pattern for defining tissue cuts based on the plurality of cut surfaces determined and positioned by the user via the user interface in the three-dimensional model of the eye;

storing three dimensional cut pattern data for controlling an ophthalmological laser device; and determining in the computer, automatically or based on user instructions, an execution sequence for the cut surfaces of the tissue cuts defined in the three-dimensional cut pattern, wherein a cut surface which, according to the execution sequence, is to be generated earlier is prevented from covering or shadowing focused radiation of the femtosecond laser pulses for generating a cut surface which, according to the execution sequence, is to be generated later, and wherein the covering or shadowing is determined on the basis of a beam cone defined by focused projection of the femtosecond laser pulses, by checking whether the beam cone for generating a cut surface which, according to the execution sequence, is to be generated later, is interrupted by a cut surface which, according to the execution sequence, is to be generated earlier.

13. The method of claim 12, wherein the at least one cut surface is defined in the computer on the basis of a user-defined cutting line and a user-defined cutting line trajectory.

14. The method of claim 12, wherein the at least one cut surface is defined in the computer on the basis of at least one surface element, which can be selected from a list of a plurality of different surface elements on the basis of user instructions.

15. The method of claim 12, further comprising determining in the computer, based on user instructions, an application element which should be applied to the eye when executing the tissue cuts.

16. A computer-implemented method of generating a three-dimensional cut pattern which defines one or more tissue cuts to be executed in a human eye by means of femtosecond laser pulses, the method comprising:

storing in a computer eye data which defines a three-dimensional model of the eye;

determining in the computer, based on the eye data and an application element which is to be applied onto the eye when executing the tissue cuts, a three-dimensional model of the eye, representing the eye in an applied application element state;

displaying the three-dimensional model of the eye in a user interface;

defining and storing in the computer at least one geometric reference in relation to the three-dimensional model of the eye;

displaying the at least one geometric reference in the three-dimensional model of the eye in the user interface;

defining in the computer, based on user instructions received via the user interface, a plurality of cut surfaces and positioning the plurality of cut surfaces in the three-dimensional model of the eye displayed in the user interface in relation to the at least one geometric reference based on user instructions for defining orientation and a three-dimensional position of the cut surface in the three-dimensional model of the eye, the three-dimensional position of the cut surface being defined by the user using positioning elements of the computer to displace the cut surface in the three-dimensional model of the eye;

repeating the defining and the positioning of cut surfaces based on user instructions, until the user indicates via the user interface that defining and positioning of a cut is complete and a plurality of cut surfaces have been defined and positioned by the user via the user interface in the three-dimensional model of the eye;

generating in the computer the three-dimensional cut pattern for defining tissue cuts based on the plurality of cut surfaces determined and positioned by the user via the user interface in the three-dimensional model of the eye;

determining in the computer, automatically or based on user instructions, an execution sequence for the cut surfaces of the tissue cuts defined in the three-dimensional cut pattern, wherein a cut surface which, according to the execution sequence, is to be generated earlier is prevented from covering or shadowing focused radiation of the femtosecond laser pulses for generating a cut surface which, according to the execution sequence, is to be generated later; and storing for the three-dimensional cut pattern data for controlling an ophthalmological laser device, and wherein the covering or shadowing is determined on the basis of a beam cone defined by focused projection of the femtosecond laser pulses, by checking whether the beam cone for generating a cut surface which, according to the execution sequence, is to be generated later, is interrupted by a cut surface which, according to the execution sequence, is to be generated earlier.

* * * * *